United States Patent [19]

Rutledge, Jr. et al.

[11] Patent Number: 4,475,404

[45] Date of Patent: Oct. 9, 1984

[54] PULL TESTER

[75] Inventors: Woodrow T. Rutledge, Jr.; Russell P. Rutledge; John E. Freeman, all of Big Spring, Tex.

[73] Assignee: Fiberflex Products, Inc., Big Spring, Tex.

[21] Appl. No.: 409,253

[22] Filed: Aug. 23, 1982

[51] Int. Cl.³ .............................................. G01N 3/10
[52] U.S. Cl. ...................................... 73/827; 73/837
[58] Field of Search ................ 73/826, 837, 49.1, 828, 73/830, 831, 834, 827

[56] References Cited

U.S. PATENT DOCUMENTS 2,884,986  5/1959  Heldenbrand .................... 73/831 X
3,690,160  9/1972  Kriesten ............................... 73/831
4,335,615  6/1982  Kalfa et al. ....................... 73/826 X

FOREIGN PATENT DOCUMENTS 1071981  5/1953  Fed. Rep. of Germany ........ 73/837

Primary Examiner—Jerry W. Myracle
Attorney, Agent, or Firm—Guy E. Matthews

[57] ABSTRACT

A device for testing the tensile strength of fiberglass rods. A hydraulic ram system applies force through specially shaped holders to the ends of fiberglass sucker rods having end connectors mounted by a combination of adhesive and compression joints.

1 Claim, 3 Drawing Figures

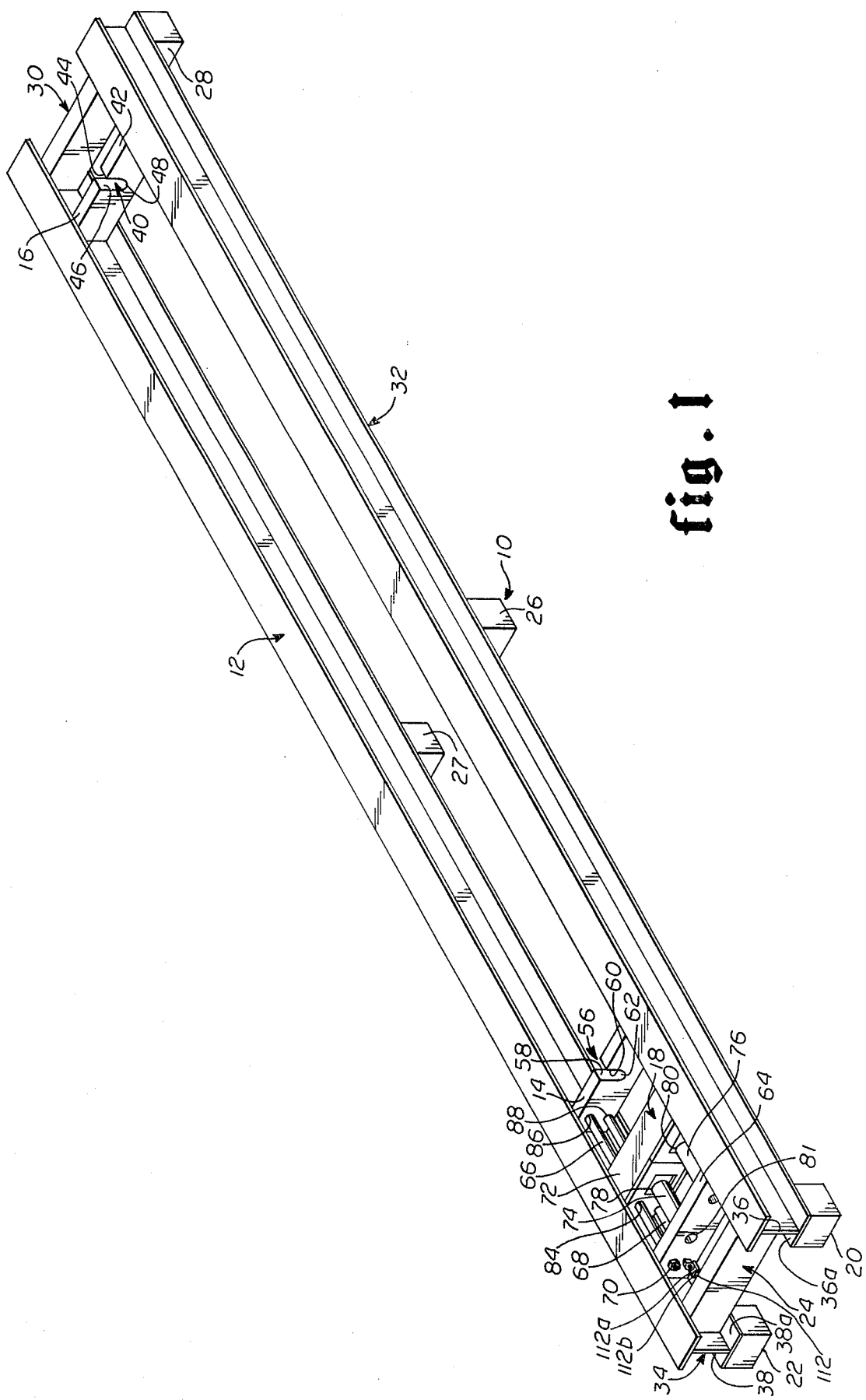

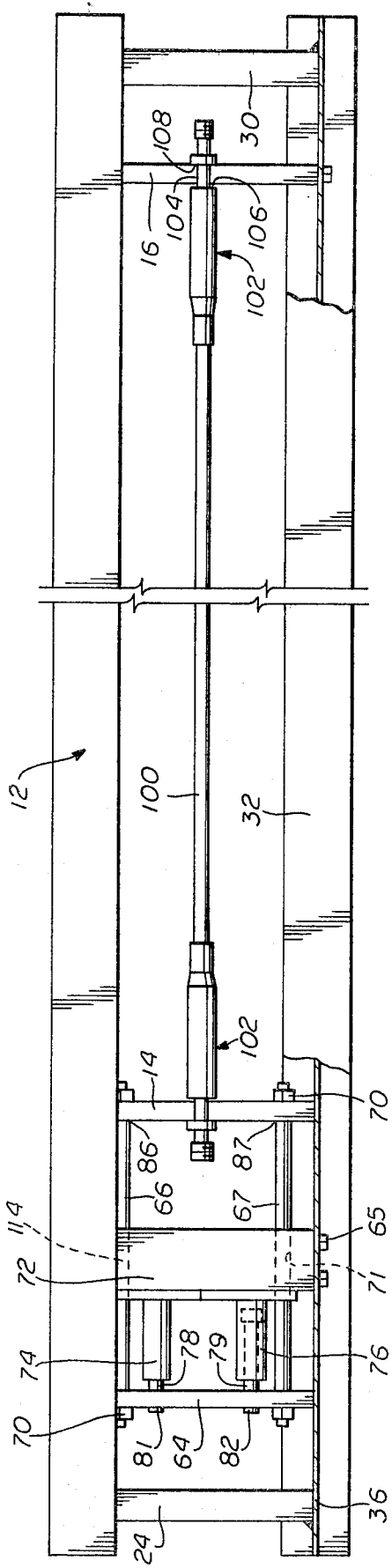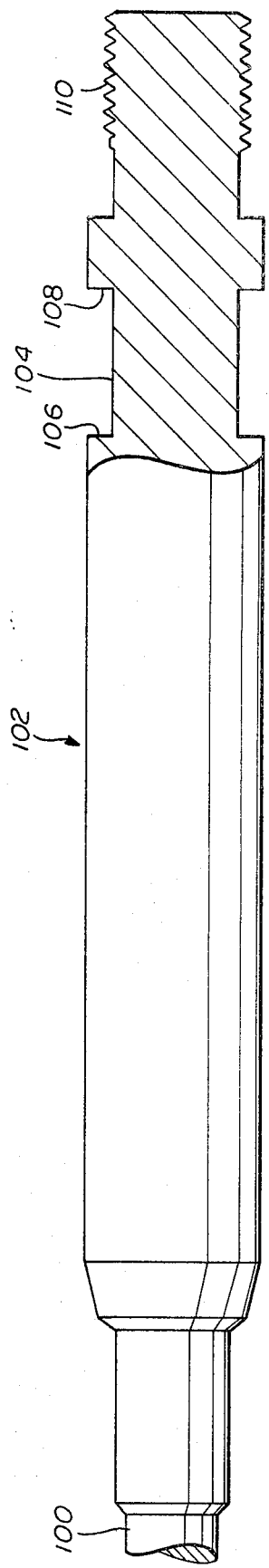

PULL TESTER

TECHNICAL FIELD

This invention relates to equipment used to pull test fiberglass rods having metal connector ends attached to the rods. More particularly, the invention relates to equipment to test both the rods and the connectors attached to the rods under tensile load.

BACKGROUND ART

Steel sucker rods have been used for decades in producing oil wells to actuate petroleum pumps located in well bores of producing, but not pressurized, oil wells. A series of sucker rods are connected together to form a string extending down into the well bore. The string is connected to a petroleum pump at the end in the well bore and to a cyclic or reciprocating drive mechanism at the well head to actuate the petroleum pump to cause oil to be pumped up the well bore and into a pipeline. Recently, steel sucker rods have been replaced in part in the well bores by sucker rods made out of other materials, such as fiberglass. See, for example, U.S. patent application Ser. No. 076,373, filed Sept. 17, 1979 by Woodrow T. Rutledge, Jr. et al entitled: "Fiberglass Sucker Rod Construction" now U.S. Pat. No. 4,360,288. The fiberglass rods are provided with end connectors of steel or other suitable material which are mounted with the fiberglass rods by a combination of adhesive and compression joints. The fiberglass sucker rods with the end connectors, like steel sucker rods, must provide tensile strength at least to the American Petroleum Institute standard of 21,000 lbs. and must withstand thousands of pounds of pressure and must be constructed to withstand the cyclic axial forces without fatigue.

The tensile strength of these rods and each connector adhesive is tested for rods manufactured by Fiberflex Product, Inc. by a tester which applies a tensile load on the rod greater than that expected in actual operation. The mechanism which tests the tensile strength of the fiberglass sucker rod and the end connector also applies the tensile force to the end connectors necessary to cause the annular wedges of cured adhesive material between the rod and the end connectors to be forced into compressive engagement with the rod outer cylindrical surface and with the connector member tapered surfaces. See U.S. patent application Ser. No. 076,373, supra at page 8, lines 1-6.

A testing method of the prior art of this type was previously used but did not contemplate nor embody the rams push plate, a stationary plate and pull rods.

DISCLOSURE OF INVENTION

The present invention provides a test device for testing the tensile strength of fiberglass rods wherein the device includes:

(1) a base;
(2) a container for holding the rod mounted on the base;
(3) a fixed holder in the container for one end of the rod;
(4) a movable holder in the container for the other end of the rod; and
(5) a force mechanism attached to the movable holder to move it toward or away from the fixed holder.

BRIEF DESCRIPTION OF THE DRAWINGS

For a further understanding of the nature and objects of the present invention, reference should be had to the following detailed description, taken in conjunction with accompanying drawings, in which like parts are given like reference numerals, and wherein:

FIG. 1 is a prospective view of the preferred embodiment of the testing unit of the present invention;

FIG. 2 is a top plane view of the apparatus of FIG. 1;

FIG. 3 is a prospective partial view of a fiberglass sucker rod; and

BEST MODE FOR CARRYING OUT THE INVENTION

Referring to FIG. 3, a partial view of sucker rod 100 is shown. Fiberglass rod 100 has at each end a normally steel receptacle 102 of which only one is shown in FIG. 3 and both in FIG. 2. At the outer ends of receptacle 102 are opposed flat surfaces 104 bounded by shoulder 106, 108 and separated by semi-circular portions 109. At the extreme ends of each receptable 102 are male threads 110 for connection to a female connector (not shown).

Referring to FIGS. 1 and 2, the testing unit for a rod 100 can be seen to comprise a base 10, a container or frame member 12 mounted on base 10, moving and fixed holders 14, 16, respectively, mounted in container 12, and a force mechanism 18 attached to the moving holder 14 and contained in container 12.

Many mechanisms for support of a box 12 by a base 10 are known in the art. See, for example, FIG. 1. In FIG. 1, base 10 includes six blocks of concrete, steel or other suitable material which support rectangular box 12. Two blocks 20, 22 are located at a first end 24 of box 12; two blocks 26, 27 are located at the approximate center of box 12; and two blocks 28 and one not shown are located at the outer end 30 of box 12. Each pair of blocks is separated, preferably, with the total end to end spacing of each pair of blocks being approximately 36 inches. It is to be understood that base 10 may be of a wide variety of components, shapes and arrangements and may be integral with container 12 without deviating from the spirit of the invention.

Box 12 is rectangular in shape having ends 24, 30 and sides 32, 34. The sides 32, 34 are, preferably, steel I beams, and ends 24 and 30 abut and are affixed to web 36, 38 of sides 32, 34 respectively.

The holding mechanism for rod 100 includes moving holder 14 and fixed holder 16. Holder 16 is rectangular in shape and is affixed to the webs 36, 38 of I beams 32, 34 and suitable means such as welding or nut and bolt near end 30. A groove 40 is cut into the top 42 of fixed holder 16. Groove 40 has vertical opposing sides 44, 46 and a bottom semi-circular troth 48. Sides 44, 46 are spaced to receive semi-circular portions 109 of rod 100. The thickness of fixed holder 16 is determined by the width of flat surfaces 104 such that shoulders 106, 108 bounding flat surfaces 104 are juxtaposed with the sides of fixed holder 16.

Moving holder 14 is of substantially the same rectangular shape as holder 16. Holder 14 also has a similar groove 56 to groove 40. Groove 56 has vertically opposed walls 58, 60 with semi-circular troth 62 at the bottom of groove 60. The dimensioning of groove 56 is substantially the same as that of groove 40. Holder 14 is located near end 24.

Holder 14 is slidable relative to I beam sides 34, 36 by fitting within the webbing of the beam and being pulled when the hydraulic system means 18 is actuated to move plate 64 which in turns mover plate 64 by hydraulic cylinder 74, 76 and then moves plate 14 through cam bore or members such as at 66.

Hydraulic system 18 includes moving plate 64 slidably mounted between I beam sides 36, 38 and a fixed plate 72, both plates being located between holder 14 and end 24. Fixed plate 72 is secured to webs 34, 38 by bolts 65 or other suitable means and faces holder 14. Moving plate 64 is slidably mounted between plate 72 and rests on internal webbing 36A and 38A.

Hydraulic system 18 further includes four rods 66, 67, 68 and one not shown. The rods 66, 67, 68 and the one not shown extend from plate 64 to moving holder 14 through bores 71 in fixed plate 72. The rods 66, 67, 68 and the one not shown are secured at ends 70 to plate 64 and moving holder 14. Dual hydraulic cylinders 74, 76 are mounted to plates 78, 80 respectively on fixed plate 72. Piston 78, 79 reciprocate in cylinders 74, 76 respectively and are securely attached at ends 81, 82 respectively to moving plate 64.

Ram systems 74, 76, 78, 79 are, preferably, two 6 inch rams with a hydraulic system not shown. Each ram is capable, preferably, of developing 125,000 pounds of force. The holders 14, 16 and plates 64, 72 may be of any suitable material, such as steel. The rods 66, 67, 68 and the one not shown may be of any suitable material, such as steel.

In addition, the ram systems are connected to a suitable gauge means 114 for measuring the tensile strength of each rod and receptable pulled and a suitable electrical trip switch 112 having leads 112a and 112b for releasing the pull tension by forcing fluid against the opposite sides of each of the double acting hydraulic rams.

In operation, fiberglass rod 100 is mounted between holders 14, 16. A hydraulic unit (not shown) then supplies cylinders 74, 76 with sufficient pressure to develop up to 250,000 pounds of force between plates 64, 72 via pistons 78, 79. The pistons 78, 79 exert this force against plates 64, 72 thereby driving plate 64 towards end 24. Rods 66, 67, 68 and the one not shown attached to plate 64 and holder 14 are pulled towards end 24 by plate 64, thereby pulling holder 14 towards end 24. The shoulders 106, 108 of fiberglass rod 100 and fixed holder 16 prevent rod 100 mounted in grooves 48, 62 from following. Therefore a tensile force is exerted on the rod 100 because holder 16 is stationery. The load may be varied by varying the amount of pressure exerted by the hydraulic unit on the rams.

Although the system described in detail supra has been found to be most satisfactory and preferred, many variations in structure are possible. For example, the dimensions of the box may be adapted to other lengths and sizes of rod. Further, the hydraulic system could be adapted for either smaller or greater pressure conditions. The options enumerated above are merely exemplary of the possible changes of variations.

Because many varying and different embodiments may be made within the scope of the inventive concept herein taught, and because many modifications may be made in the embodiments herein detailed in accordance with the descriptive requirements of the law, it should be understood that the details herein are to interpreted as illustrative and not in a limiting sense.

What is claimed is:

1. A test system for pull testing the tensile strength of fiberglass sucker rods and end connectors adhesively connected thereto, said system acting to apply a tensile load greater than that expected in actual operation, and a tensile force to said end connectors necessary to cause the annular wedges of cured adhesive material between said rod and said end connectors to be forced into compressive engagement with the rod outer cylindrical surface with the connector member tapered surfaces, said system comprising:

a containment member, including a base;

holding means for holding the fiberglass sucker rod in said containment member, said holding means including a first member fixed to said containment member and a second member movable relative to said containment member; and movement means for moving said second member away from said first member, said movement means including a first plate fixed to said containment member;

a second plate movable relative to said containment member;

force means for forcing said second plate away from said first plate;

connection means for connecting said second plate with said second member;

means for measuring the tensile pressure caused by said force means;

means for switching said force pressure to the off position when said second plate has moved a predetermined distance.

* * * * *